United States Patent [19]

Smolen

[11] 4,335,438
[45] Jun. 15, 1982

[54] METHOD AND APPARATUS FOR AUTOMATIC DISSOLUTION TESTING OF PRODUCTS

[76] Inventor: Victor F. Smolen, 227 Timbercrest Rd., West Lafayette, Ind. 47906

[21] Appl. No.: 141,093

[22] Filed: Apr. 17, 1980

[51] Int. Cl.³ .................... G06F 15/46; G01N 31/00
[52] U.S. Cl. ............................ 364/497; 23/230 R; 73/432 R; 364/162; 364/550; 422/81
[58] Field of Search ............ 364/114, 497, 499, 500, 364/550, 108, 510; 73/432 R, 53, 61 R; 23/230 A, 230 B, 230 R; 422/81, 103, 62, 68

[56] References Cited

U.S. PATENT DOCUMENTS

| | | | |
|---|---|---|---|
| 3,223,486 | 12/1965 | Holl, Jr. et al. | 23/230 R |
| 3,467,500 | 9/1969 | Wilkinson | 23/230 R |
| 3,545,864 | 12/1970 | Dibbern | 23/230 B |
| 3,684,448 | 8/1972 | Stricker | 23/230 B |
| 3,791,221 | 2/1974 | Kirschner et al. | 73/432 R |
| 3,791,222 | 2/1974 | Goodhart et al. | 73/432 R |
| 3,801,280 | 4/1974 | Shah et al. | 23/230 R |
| 4,158,694 | 6/1979 | Bischoff et al. | 422/81 |

OTHER PUBLICATIONS

Smolen, "Theoretical and Computational Basis for Drug Bioavailability Determinations Using Pharmacological Data . . .", J. Pharmacokinetics and Biopharmaceutics, vol. 4, No. 4, pp. 355-375, 1976.
Smolen et al., "Optimally Predictive in Vitro Drug Dissolution Testing for in Vivo Bioavailability"; J. Pharm. Sci., vol. 65, No. 12, pp. 1718-1724; Dec. 1976.
Smolen et al., "Predictive Conversion of in Vitro Drug Dissolution Data into in Vivo Drug Response . . .", J. Pharm. Sci., vol. 66, No. 3, pp. 297-304, Mar. 1977.
Smolen et al., "Predicting the Time Course of in Vivo Bioavailability from in Vitro Dissolution Tests . . ."; Pharm. Tech.; Jun. 1979, pp. 89-102.

Primary Examiner—Errol A. Krass
Attorney, Agent, or Firm—James F. Cottone

[57] ABSTRACT

A method and apparatus for optimally performing dissolution testing of pharmaceutical dosage forms, agricultural products, and components of industrial products wherein the method uses dissolution profiles from a known drug dosage form, or product, as reference data for a predictive process; and the apparatus is organized to carry out the method via both closed loop and open loop operating modes under the control of a central processor. An illustrative embodiment teaches the serial usage of the two operating modes in a single flow-through dissolution cell configuration to optimally predict the time course of in vivo bioavailability from in vitro dissolution measurements, while an alternate embodiment teaches the use of a plurality of dissolution cells and the simultaneous use of the closed and open loop operating modes to implement an Internal Standard capability. Additionally, an optimally adaptive capability is provided in the dissolution testing process via a random input modeling mode of operation.

15 Claims, 5 Drawing Figures

METHOD AND APPARATUS FOR AUTOMATIC DISSOLUTION TESTING OF PRODUCTS

BACKGROUND OF THE INVENTION

1. Field of the Invention

The present invention relates generally to the field of automatic dissolution testing of products whose solubility and dissolution rate properties affect product performance, and more specifically to the optimal prediction of product dissolution characteristics using known product data as a reference for a feedback controlled apparatus.

The methods disclosed and the electronically controlled apparatus described are presented in connected with in vitro dissolution testing of pharmaceutical drug dosage forms to predict in vivo bioavailability. However, both the methods and apparatus taught are equally applicable to dissolution testing of agricultural products formulated as controlled release herbicides, insecticides, fertilizers, and the like; and are further applicable to the dissolution testing of components of industrial products including solid materials whose solubility properties depend on a wide variety of factors.

2. Description of the Prior Art

Dissolution testing of components of industrial products whose solubility and dissolution rate properties affect product performance can be used as a screening and quality control tool. The solubility properties of solid materials can depend on polymorphic crystalline form, crystal habit, crystal shape, particle size and particle size distribution, and state of solvation. A simple and rapidly performed dissolution test can substitute for the determination of these physical properties by more time consuming and expensive methods such as x-ray crystallography, differential thermal analysis, microscopy, etc. The materials are instead determined as to whether they conform to a dissolution rate standard under specified conditions and in relation to a known reference sample of the same material characterized by the above physical properties and possessing the desired dissolution rate and solubility characteristics.

The broad technique of determining dissolution rate properties is especially of interest in the testing of drug products where the therapeutic performance of drugs is closely related to the drug dissolution properties. Seemingly minor changes in drug product formulation, as well as the inadvertent variation in materials and manufacture that can occur between batches of the same product formulation, can influence the therapeutic performance of drugs. In vivo bioavailability testing of drug products in humans provides the most reliable means of ensuring bioequivalence. However, it is impractical to perform the extensive and expensive human testing that would be routinely required. Large numbers of human subjects would be placed at risk if such studies were conducted. Bioavailability testing in which humans are used as test subjects can be minimized by the development and implementation of in vitro dissolution standards that reflect in vivo drug-product performance. In vitro bioequivalence requirements have been established for some drugs such as digoxin. From among the various chemical and physical tests that can be performed on drug solids in vitro for correlating or predicting a drug product's in vivo bioavailability behavior, dissolution testing is the most sensitive and reliable. The correlative relationships most commonly reported between the vitro dissolution and in vivo bioavailability are of the single-point type: the percentage of the drug dissolved in a given time (or the time it takes to dissolve a given percentage of the drug in vitro) and some univariate characteristic of the drug product's in vivo response versus time profile (such as the peak blood level, the time required to reach the peak or 50% of the peak, or the area under the blood-level curves) are correlated. The selection of in vitro dissolution and in vivo bioavailability parameters for such single-point correlations is frequently arbitrary, and the results can be misleading. Obviously, it would be preferable to predict the entire average blood level, urinary recovery rate, pharmacological-response-time, or drug absorption rate vs. time profile that would be elicited by a drug product in a panel of human subjects rather than merely to correlate univariate characteristics of the dissolution profile with an in vivo bioavailability parameter. In all cases, however, the fidelity of the in vitro dissolution results in correlating and in predicting in vivo drug-product bioavailability depends upon the dissolution-test process variables, such as the dissolution-medium composition, the solubility volume of the medium (sink conditions that determine the extent to which the medium becomes saturated with the drug), and the agitation rates (stirring or flow rates). An improper choice of these process variables (e.g., an excessively high rate of agitation) can mask significant bioavailability differences among drug products. On the other hand, the dissolution test can be overly sensitive in detecting differences that are negligible in vivo. In the former case, using such improper dissolution-test parameters would result in the marketing of therapeutically ineffective drug products. In the latter case, the result would be the discarding of drug products that are entirely satisfactory in terms of in vivo performance. Serious economic losses could result from the use of an overly sensitive in vitro dissolution test for lot-to-lot reproducibility testing of drug products. Therefore, whether the dissolution test is being used as a quality control tool, as an in vivo bioequivalency requirement for multisource generic drug products, or as a substitute for human bioavailability testing during the development of new drug-product formulations, it is imperative that the dissolution test provide predictive results that are biologically relevant.

Developing drug-product dissolution tests that predict the time course of drug-product bioavailability can be fraught with pitfalls, some of which may be avoided through knowledge and consideration of the physiochemical properties of the components of the drug product and the biological processes and conditions operative in the release of the drug from the gastrointestinal tract and its subsequent absorption. However, it is not only futile, but also unnecessary to attempt to reproduce the complex of biological factors operating in vivo in the effort to develop a satisfactory in vitro bioavailability test, although such attempts have been made. The devices that resulted from these efforts are of value now only as museum pieces. It would, however, be imprudent to ignore such knowledge when it can be used advantageously to circumvent a problem in the design of a dissolution test.

There are two possible general approaches to developing in vivo relevant drug product dissolution tests. Both approaches seek to predict the entire time course of average blood levels that would be observed for a drug product in a panel of human test subjects. In this way, the dissolution test serves as a substitute for human testing.

The first approach is a computational method that maximizes the amount of information that can be obtained from conventional methods of in vitro dissolution testing. Used most frequently are the USP rotating-basket apparatus, the FDA paddle method, the stationary-basket/rotating filter apparatus, Sartorious solubility and absorption simulators (Sartorius, Incorporated, Hayward, Calif.), and column-type flow-through assemblies. The last of these devices offers advantages with regard to the definition, flexibility of control, standardization, and reproducibility of process variables. This apparatus has been used by the inventor of the present invention to demonstrate the second approach to predicting in vivo blood-level curves that emerge from the apparatus in the form of dissolution rate versus time profiles.

Since the computational approach with conventional apparatus depends upon the relatively arbitrary selection of process variables, its usefulness is limited. However, using feedback control to continuously vary the process variables, as described below, obviates this problem. For a more complete treatment of the mathematical (and theoretical) aspects of the dissolution, the interested reader is directed to three papers co-authored by the inventor. These are: V. F. Smolen et al., "Optimally Predictive In Vitro Drug Dissolution Testing for In Vivo Bioavailability," J. Pharmaceutical Sci., Vol. 65, No. 12, pp. 1718-1724, December 1976; V. F. Smolen et al., "Predicting the Time Course of In Vivo Bioavailability From In Vitro Dissolution Tests: Control Systems Engineering Approaches," Pharmaceutical Technology, pp. 89-102, June 1979; and V. F. Smolen et al., "Predictive Conversion of In-Vivo Drug Dissolution Data into In Vivo Drug Response Versus Time Profiles Exemplified for Warfarin," J. Pharmaceutical Sci., Vol. 66, No. 3, pp. 297-304, March 1977.

The present invention is directed to an improved method and apparatus for carrying out the dissolution approach to optimally predicting in vivo drug bioavailability from pharmaceutical dosage forms, and other applications of dissolution testing.

SUMMARY OF THE INVENTION

It is therefore a primary object of the present invention to provide improved methods and apparatus for performing dissolution testing of pharmaceutical dosage forms, agricultural products, and components of industrial products whose solubility and dissolution rate properties affect product performance.

Another object of the present invention is to provide improved methods and apparatus for predicting in vivo bioavailability of drug dosage forms from in vitro dissolution testing.

Another object of the present invention is to provide methods and apparatus for dissolution testing of industrial products, including drug dosage forms, agricultural products, and the like, wherein a closed loop control process is first used to initialize the control loop process variables while operating on known reference data, and an open loop control process is then used to perform the predictive process using the process variables previously derived.

Another object of the present invention is to provide methods and apparatus for dissolution testing of a plurality of industrial products, including drug dosage forms, agricultural products, and the like, simultaneously, using an operating mode wherein closed loop and open loop control processes are accomplished concurrently using a known product formulation and its corresponding dissolution profile as reference data, to implement an Internal Standard operating mode.

A still further object of the present invention is to provide an improved dissolution testing apparatus including a dissolution cell having proportional agitation means and to further provide an optimally adaptive capability into the dissolution testing process via a random input modeling mode of operation.

BRIEF DESCRIPTION OF THE DRAWINGS

Additional objects and advantages of the invention will become apparent to those skilled in the art as the description proceeds with reference to the accompanying drawings wherein.

DETAILED DESCRIPTION OF THE PREFERRED EMBODIMENT

Figure 1:
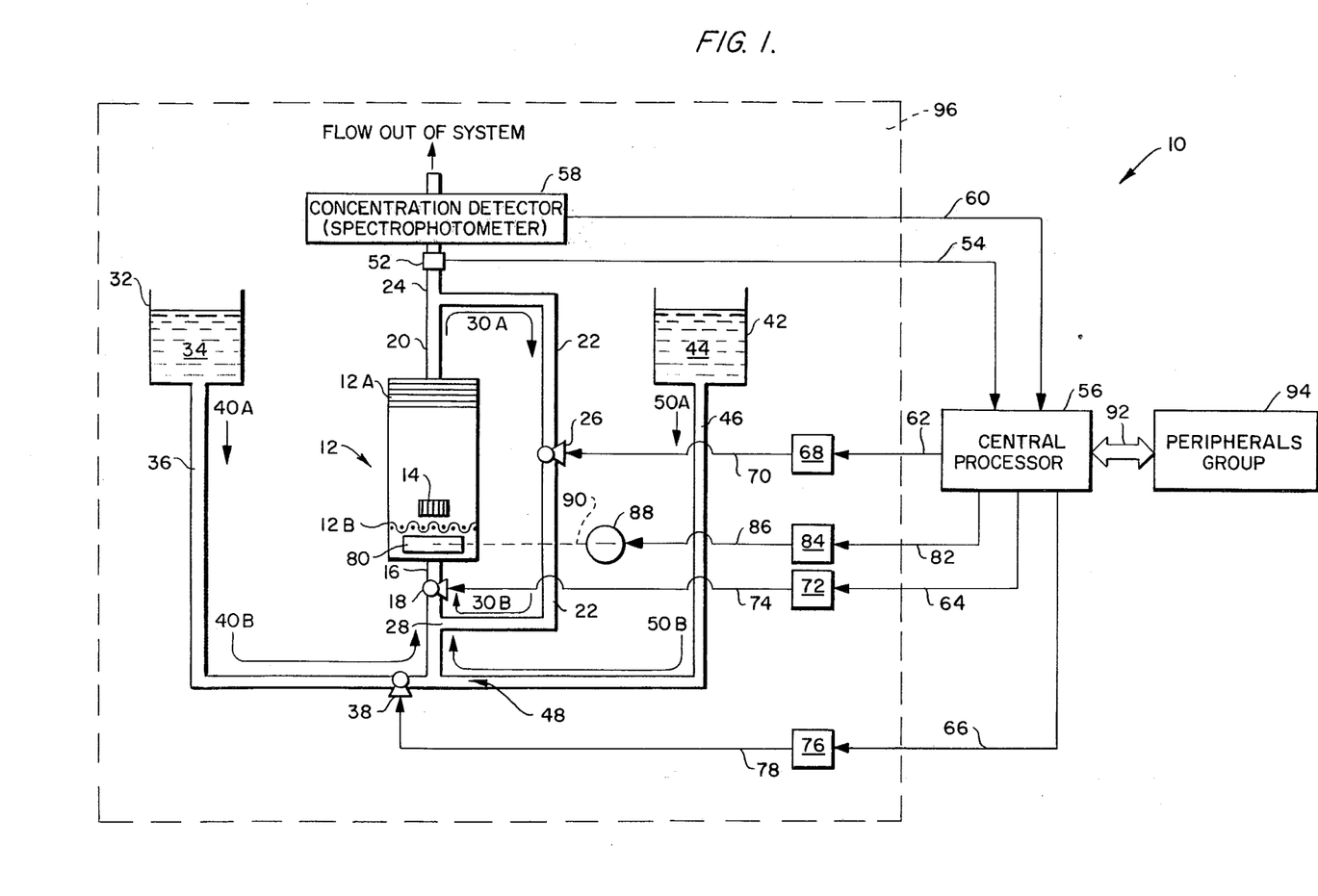
FIG. 1 is an overall block diagram of the automatic dissolution testing system according to the present invention.

Referring now to FIG. 1, there is shown an overall block diagram of the automatic flow-through dissolution testing system according to the present invention. For simplicity of exposition the various elements are not shown to scale, and the embodiment shown is a basic one. The descriptions throughout this specification are expressed in terms of the testing of a pharmaceutical drug dosage form, and the language is accordingly specific to this usage. Of course, the embodiments disclosed are illustrative and could readily be adapted for use with agricultural products, or with controlled release components of industrial products generally. The overall system 10 is shown as comprised of a basic dissolution cell 12 in which is positioned a specimen of the drug product 14 undergoing evaluation. The cell 12 has a filter membrane 12A and filter screen 12B, and is provided with a flow of various dissolution liquid via a cell input line 16 under the influence of a primary pump 18. Output from the dissolution cell 12 is carried by a cell output line 20 and is routed first via the upper portion of a recirculation line 22, and thereafter via a system output line 24. Within the recirculation line 22 is a recirculation pump 26 which propels the liquid therein into the lower portion of the recirculation line 22, and thereafter into a feeder line 28, which serves as an input to the primary pump 18. The two arrows 30A and 30B show the direction of flow in the recirculation line 22 under the influence of the recirculating pump 26.

A first reservoir 32 is used to contain a supply of a first dissolution medium 34, which is fed via a line 36 to the dissolution cell 12. The first dissolution medium 34, hereinafter alternately called the acid medium, if fed to the feeder line 28 under the influence of a pump 38. The flow direction of the acid medium 34 is shown by the flow arrows 40A and 40B. A second reservoir 42 is used to contain a supply of a second dissolution medium 44, hereinafter alternately called the alkaline medium 44. The alkaline medium 44 is fed via a line 46 and a check valve 48 to the feeder line 28, and subsequently through the primary pump 28 to the dissolution cell 12. The flow direction of the alkaline medium 44 is shown by the flow arrows 50A and 50B. As will be discussed in detail below, the flow path 40B of the acid medium 34 is due to the presence of the check valve 48, and the flow path 50B of the alkaline medium 44 is due to the dynamics of the action of the two pumps 38 and 18.

The system output line 24 serves to conduct the flow of the processed media containing the desired concentration of the dissolved drug product out of the system, and further supports two key system measurements. A flow measurement device 52, serially positioned in the output line 24, provides a quantitative measurement of a liquid flow rate via a group of lines 54 to a central processor 56. (Alternatively, this flow rate may be obtained electronically as the difference in control signals to the primary pump 18 and the recycle pump 26.) A spectrophotometer 58, also serially positioned in the output line 24, provides a periodic (or continuous) measurement of the drug concentration in the output flow, and routes this measurement via a group of lines 60 to the central processor 56. Pumps 18, 26 and 38 are of the positive displacement peristaltic type and are capable of producing precisely controlled flow rates in the range of 0.2 to 140 ml per minute when properly controlled. The central processor 56 provides this control via signals on three groups of lines 62, 64 and 66 which modulate the excitation to the pumps as follows. Control signals on the line 62 are applied to a pump speed modulator 68, which in turn controls the excitation of the pump 26 via the lines 70; control signals on the lines 64 are applied to a pump speed modulator 72, which in turn controls the excitation of the pump 18 via the lines 74; the control signals on the line 68 are applied to a pump speed modulator 76, which in turn controls the excitation to the pump 38 via the lines 78. In addition to the above three control signals, the central processor 56 further provides control signals to an agitation means comprised of a stirring paddle 80 located within the dissolution cell 12 and positioned below the filter screen 12B. These control signals are provided on a group of lines 82 to an interface device 84. An output from the interface device 84 is applied via lines 86 to an agitation motor 88, which in turn activates the stirring paddle 80 via the mechanical linkage shown as dashed lines 90. A group of control and data lines 92 interconnect the central processor 56 with a number of supporting units shown as a peripherals group 94. Included within this group 94 would be a data recorder 94A (analog and/or digital), an output printer 94B, and input keyboard 94C, and other well known and conventional devices. An overall measurement block 96 identifies those elements considered to be measurement apparatus, as compared to the remaining elements—56 and 94—which may be considered to be the signal processing and control portions of the system.

In use, the system of FIG. 1 carries out the dissolution testing under the control of the central processor 56 as follows. By way of a brief overview, the system shown is operable in two modes, the first being a simulative (or closed loop mode) and the second being a predictive (or open loop mode). First, a known drug dosage form is used to "calibrate" the apparatus by operating it in the closed loop mode using known in vivo data (as played back from the recorder 94A) on the particular drug dosage form to optimize a number of parameters (hereinafter alternately referred to as the process variables) within the central processor 56. An iterative optimizing process may be used to systematically modify the process variables until the difference between the measured (in vitro) data and the known (in vivo) data are minimized, and independent of time. Secondly, predictive tests of unknown drug dosage forms are performed using open loop control of the apparatus employing the previously determined values of the process variables. To accomplish these steps, control (proportional, differential and integral) is exercised over one or more of the process variables determined by: (1) the composition; (2) the recycle flow of the dissolution medium; (3) the total flow rate of the dissolution medium; and (4) the rate of agitation within the dissolution cell.

During the course of the closed loop phase of the operation, a change in the medium pH can be used to simulate the in vivo change from the stomach to the duodenum, and the recycling of the medium to dissolution cell 12 allows variable sink conditions to be achieved to simulate the existing in vivo conditions due to differing barrier properties of drug absorbing biological membranes. Resistance to biological absorption is simulated by mixing the fresh medium with the solution leaving the cell. The recycling of solution through the dissolution cell in this manner decreases the driving force for dissolution. Upon establishing a desired constant flow rate at the outlet of the dissolution cell as determined by the flow measuring device 52, the time varying recycle flow rate and a changing flow from the gastric and intestinal juice reservoirs (i.e., first and second dissolution medium 34 and 44) are initiated. The spectrophotometer 58 provides a measurement of the concentration of the drug in the liquid leaving the cell. An alternate configuration may include placing the spectrophotometer on the recycle flow line. This measured concentration value is compared within the central processor 56 with the known in vivo bioavailability rate, blood level, urinary recovery rate, or pharmacological response versus time profiles being simulated. Any error signal produced is converted within the central processor 56 so as to optimize the process variables driving the error signal to a minimum value.

Figure 2:
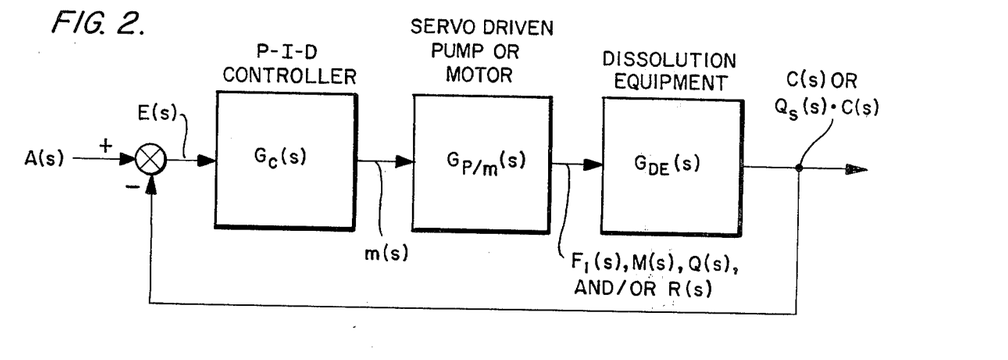
FIG. 2 is a simplified block diagram of the closed loop programmed control of the automatic dissolution testing system.
Figure 3:
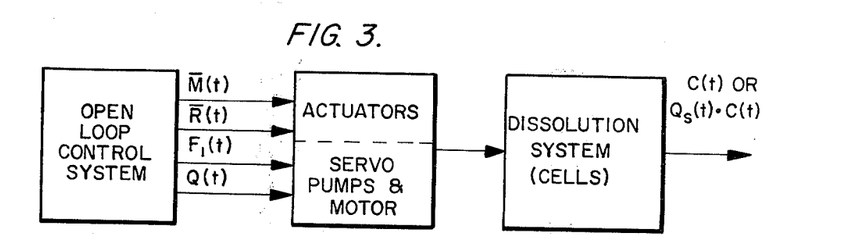
FIG. 3 is a simplified block diagram of the open loop control system implemented in the automatic dissolution testing system.

A detailed description of the operation of this system of FIG. 1 is facilitated with additional reference to the block diagrams of FIGS. 2 and 3. Additionally, an illustrative hardware configuration is described in connection with the improved control system shown in FIG. 5. FIG. 2 shows a block diagram for the closed loop control of the dissolution testing system in the simulative mode; while FIG. 3 shows a block diagram for open loop control of the dissolution testing system in the predictive mode. Both the time variable form: $R(t)$, and the transform variable form: $R(s)$ of the system parameters will be used herein (interchangeably as required) as is well known in the control system art. The following process variables are applicable:

$Q(t)$ = volumetric flow rate (milliliters per minute)
$Q_A = Q/A_C$ = velocity through the cell (centimeters per minute)
$A_C$ = cross-sectional area of the cell (square centimeters)
$R(t)$ = volumetric flow of recycle (milliliters per minute); i.e., it can be a constant or time-varying quantity
$M(t)$ = stirring rate within one dissolution chamber $F_1(t)$ = fraction of the solvent which is drawn from the reservoir containing, for example, simulated gastric juice, water, or an organic solvent (34 of FIG. 1)

$F_2(t)$ = fraction of one solvent which is drawn from the reservoir containing, for example, simulated intestinal juice, 1.0 normal sodium hydroxide, or an organic solvent (44 of FIG. 1).

The dissolution process extant within the system of FIG. 1 may commonly be described by a simple diffusion layer model:

$$dw/dt = DS/T(C_s - C)$$

where dw/dt = dissolution rate (milligrams per minute)

D = diffusion coefficient for the solvent and solute under consideration (square centimeters per minute)—affected by dissolution media composition S = surface area for dissolution (square centimeters)—an intrinsic property of the material (dosage form) being tested $C_s$ = concentration of solute required to saturate the solvent (milligrams per milliliter)—affected by dissolution media composition C = actual solute concentration in solution (milligrams per milliliter)—affected by recycle flow and total volume flow T = effective thickness of the film or diffusion layer (centimeters)—affected by agitation rate and total volume flow rate.

The relationship between variables in the diffusion layer equation and the process variables are seen as given for a fixed value of $A_C$:

T = a function of Q and agitation rate

C = a function of the volume of the dissolution chamber, V, and the volumetric flow rate, Q, i.e., the residence time, V/Q, and the flow of recycle, R or R(t). To avoid changing the volume of the dissolution chamber by changing its length to change C, this could also be effected by changing the recycle flow $C_s$ = a function of the properties of the solvent. For example, using simulated gastric and intestinal juices mentioned previously, the process variables to be manipulated here are $F_1$ and $F_2$. The variables D and $C_s$ are obviously affected by the solvents used and the relative proportions of each composing the dissolution medium at any time. When the solvent mixture is specified, D and $C_s$ are also reflective of the properties of the solid being dissolved.

S = in addition to being a function of Q, a function of the initial amount of drug, $m_o$, and the physical properties of the solid. Once these variables are fixed, i.e., once a drug and a dosage form are decided upon, the time course of S as the experiment proceeds is reflective of the properties of the drug products.

Referring first to FIG. 2, closed loop operation (simulative) in its basic form is shown as having an input signal A(s)—cumulative in vivo availability—applied to an input node where it is differenced with a fed back signal C(s)—concentration of the stream leaving the dissolution cell—to produce an error signal E(s). The error signal E(s) is applied to the input of a proportional-integral-derivative (PID) controller (actually to each of four controllers as detailed in connection with FIG. 5) having the gain characteristic (alternatively transfer function) $G_c(s)$. The output from the PID controller is a signal m(s) suitable to operate the respective actuator in the system. The four actuators of FIG. 1 include three proportional controlled pumps and one proportional controlled motor. These actuators are represented simply as having a particular transfer function $G_{p/m}(s)$, whose outputs are characterized by the four process variables R(s), M(s), Q(s), and $F_1(s)$—all as described below. The process variables are applied to the dissolution equipment having a transfer function $G_{DE}(s)$ whose output is the desired parameter C(s) or $Q_s(s) \cdot C(s)$—as described below. Briefly, FIG. 2 depicts in conventional analog-like terms the simulative function of the dissolution testing system. The analog-like descriptive terminology is used for simplicity and, of course, digital embodiments may be used to implement the control loop contemplated. During this closed loop (simulative, or calibration run) operation, three key parameters within the PID controller are optimized as described below such that subsequent open loop operation as shown in FIG. 3 constitutes an optimally predictive operating mode. As shown in FIG. 3, the open loop control system block provides optimized values of $\overline{M}(t)$, $\overline{R}(t)$, $\overline{F}_1(t)$ and $\overline{Q}(t)$ to the actuators (servo driven pumps, and/or motors) which in turn impact on the dissolution cell to produce the desired output C(t) or $Q_s(t) \cdot C(t)$ as above described.

The objective of the system of FIG. 1 is to obtain results that uniformly reflect the in vivo drug availability with optimal fidelity over time and varying drug release behavior of the dosage forms. For any given set of process variables, i.e., $Q_A$, $F_1$, ($F_2 = 1 - F_1$), the closed loop operation of the in vitro testing apparatus will produce a function $Q_{s,i}(t)C_i(t)$ for each ith dosage so that the expression $[A_i(t) - [Q(t) - R_i(t)]C(t)]$ or $[A_i(t) - C(t)]$ closely approximates zero. Functions $R_i(t)$, $M_i(t)$, $Q_i(t)$ and $F_{1i}(t)$ will be obtained for each dosage form of the drug tested that was chosen to possess different drug release dynamics. These functions can be read out by the central processor 56 onto magnetic tape, stored on magnetic disc, or in the central memory of the microprocessor during the closed loop operation of the apparatus.

At this stage, the apparatus merely simulates the A(t) functions determined from in vivo experimentation. Analog $R_i(t)$ function signals recorded on magnetic tape for each dosage form can be conveniently processed on the central processor 56 and their values can be averaged, over dosage forms, at each time to obtain an average, $\overline{R}(t)$ function representing the mean behavior of all dosage forms included in the closed loop operations. A second set of open loop runs must then be performed for each dosage form with the $\overline{R}(t)$, $\overline{M}(t)$, $\overline{F}_1(t)$, and $\overline{Q}(t)$ functions programmed to control the process variables. The number of closed loop runs performed on different dosage forms of the same drug and the resulting number of $C_i(t)$ functions and the corresponding number of $R_i(t)$, $M_i(t)$, $Q_i(t)$ and $F_{1i}(t)$ process variables included in the $\overline{R}(t)$, $\overline{M}(t)$, $\overline{Q}(t)$ and $\overline{F}_1(t)$ functions will depend on the properties of any specific drug and the drug release characteristics of the dosage forms being tested. If the dynamics of the in vivo and in vitro system approximate linear behavior, then only one reference dosage form is required. When appropriate, an objective function $F_o$ can be formed from the $\overline{M}(t)$, $\overline{F}_1(t)$, $\overline{Q}(t)$, $\overline{R}(t)$, $C_i(t)$ and A(t) functions. A minimal value of the objective function is achieved by systematically selecting different solvents, geometries of the agitator, or if one or more process variables are kept constant, different fixed values of the process variables not allowed to continuously vary with time. A minimum value of the objective function corresponds to optimal open loop operation of the apparatus under such conditions. As mentioned, various means can be implemented to control the recycle flow dynamics.

The system of FIG. 1 should be operated in the simplest manner that provides acceptable in vitro results with regard to in vivo drug availability behavior. To determine the magnitude of sensitivity of the fidelity of the test to different operating conditions, the test can be initially performed in successive phases of increasing complexity and equipment requirements.

Phase I can be performed without any automatic control, using fixed, time invariant, values of the process variables, M, $F_1$, Q, and R. An optimal composition and pH of the dissolution medium may be found and thereafter maintained constant.

Phase II can be performed similarly to Phase I but with the inclusion of automatic control of M(t) as a process variable.

Phase III can employ automatic computer control of a time-varying dissolution media composition $F_1(t)$ in addition to M(t).

Phase IV can add R(t) as an automatically controlled process variable.

Phase V can utilize M(t), $F_1(t)$, R(t) and Q(t) as automatically controlled process variables.

The order in which automatic control of the process variables is introduced depends on the properties of the drug, e.g., such as its solubility and intrinsic dissolution rate in different solvents.

These submodes of operation can be repeated for different dosage forms of the same drug to obtain the optimal conditions over all reference dosage forms. The simplest mode of operation possessing an acceptable fidelity would then be chosen for future studies with the drug.

For a somewhat more comprehensive description of the mathematical factors involved in the above, the interested reader is referred to the aforementioned 1976 article authored by the inventor. A more theoretical treatment of the relationship summarized above is also contained in an additional paper—V.F.Smolen, "Theoretical and Computational Basis for Drug Bioavailability Determinations Using Pharmacological Data II Drug Input ⇌ Response Relationships,"J. Pharmacokinetics and Biopharmaceutics, Vol. 4, No. 4, pp. 355-375, 1976.

Figure 4:
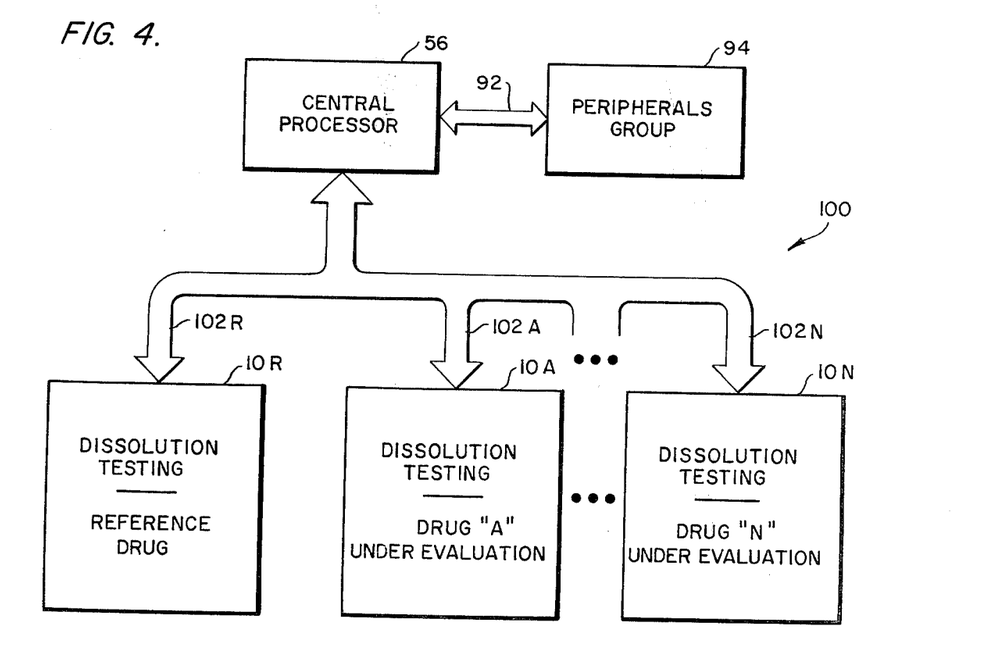
FIG. 4 is an overall block diagram of the dissolution testing system expanded to show operation in the Internal Standard mode.

Referring to FIG. 4, there is shown an overall block diagram of an alternate embodiment of the present invention directed to producing the desired predictive dissolution profile action in an Internal Standard operating mode. The embodiment shown is particularly advantageous in the testing of a number of drug dosage forms simultaneously—by comparison to a reference drug dosage form—and may be used for simultaneously testing large batches of a single drug dosage form, or of simultaneously evaluating a number of different drug dosage forms. The apparatus is basically a parallel arrangement of a plurality of single flow-through dissolution systems as shown in FIG. 1, using a single central processor/peripheral for control. The Internal Standard system 100 is shown as comprised of the elements of the embodiment of FIG. 1, in the form of a central processor 56 interconnected with a peripherals group 94 via a group of lines 92. A trunk of input/output lines 102 from the central processor 56 are routed to a reference dissolution testing subsystem 10R, via a group of input/output lines 102R; and to a first unknown dissolution testing subsystem 10A via a group of output lines 102A; and further to an "Nth" unknown dissolution testing subsystem 10N via a group of output lines 102N. The number of independent dissolution subsystems may be fairly large—a dozen, or more—being limited by purely perfunctory considerations such as cost and convenience in usage. With continued reference to FIG. 4 and occasional reference to FIG. 1, the subsystems 10R, 10A, 10N (of FIG. 4) may be identical to the measurement block 96 (of FIG. 1). The subsystem 10R, in combination with the central processor 56, the peripherals groups 94 and the interconnecting lines 92, 102 and 102R constitute a dissolution testing system identical to that of FIG. 1, operating in the closed loop mode of operation as previously described. The subsystems 10A-10N function in the open loop mode as previously described. The primary operating difference is that the N subsystems containing an unknown drug dosage form and operating open loop are controlled simultaneously by the identical control signals being generated by the control processor 56 responsive to the output measurements made on the reference dissolution cell, as compared to the reference drug in vivo dissolution profile. Thus, the in vivo dissolution profile being outputted by the recorder 94A as a time series of known data, in combination with a time series of control signal values produced by the central processor 56 serves as an Internal Standard in the sense that the predictive profiles are produced in the open loop mode by signals which are simultaneously being produced by closed loop mode of operation using a reference drug and data as the basis. A cursory review of the operation of the basic embodiment of FIG. 1, as compared with that of FIG. 4, will reconfirm that only comparatively minor differences in operation of the subsystems are involved. For example, the subsystems 10A-10N have no need to perform the measurement of flow rate and drug concentration in their output lines. Only the subsystem 10R requires that information. In the interest of the uniformity of apparatus, and as a means of providing additional versatility to the Internal Standard system 100, any or all of the subsystems 10A-10N may include the components required to measure these output parameters and provide related signals to the central processor 56. In this latter case, the central processor 56 is merely instructed to ignore the specific output data produced by those particular subsystems which are to be operated open loop.

Summarizing, the Internal Standard embodiment of FIG. 4 includes the signal processing elements (the central processor 56 and peripherals group 94) of FIG. 1 as described in more concrete terms in connection with the embodiment of FIG. 55, along with a plurality of the measuring blocks 96 of FIG. 1. Of the number of measuring blocks, one (subsystem 10R) serves as a reference subsystem and operates in a closed loop mode as described in connection with FIG. 2 with the signal processing elements, while the remainder (subsystems 10A to 10N) are controlled by the signal processing elements in the open loop mode as described in connection with FIG. 3. Thus, the plurality of subsystems 10A-10N each produce a predictive dissolution profile of a separate drug dosage form while all are referenced to a single reference drug dosage form.

Figure 5:
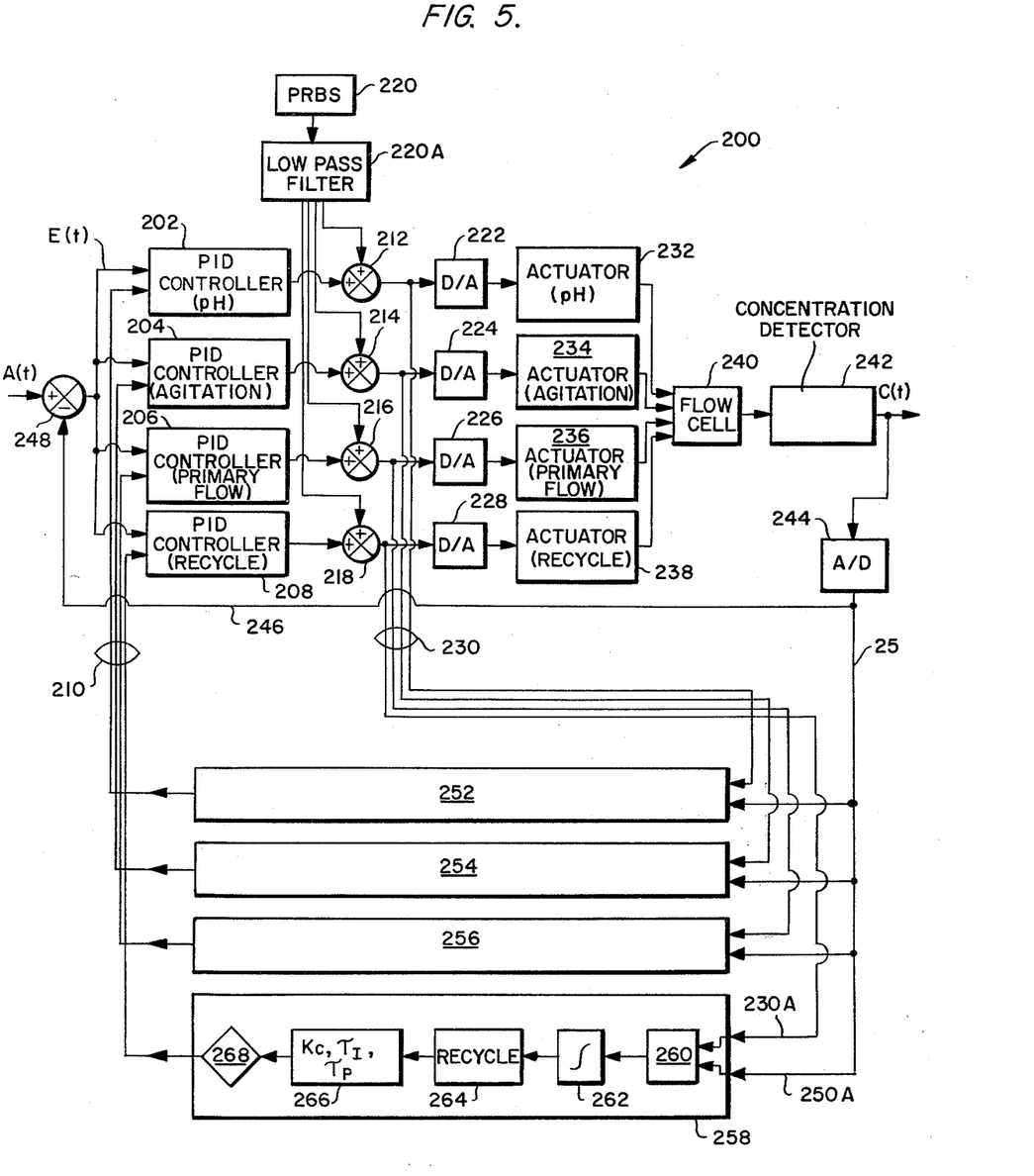
FIG. 5 is an overall block diagram of the closed loop control system for use with an improved bioavailability predictive embodiment of the present invention.

Referring now to FIG. 5, there is shown a block diagram of an improved control system for use with the dissolution testing system 10. The improved control system 200 inserts an optimally adaptive capability into the dissolution testing process via a random input modeling (RIM) mode of operation. Briefly, this mode impacts on operation in the closed loop mode wherein the average in vivo human drug response profile input, A(t), for a reference drug product is reproduced as the concentration vs. time profile, C(t), output from the apparatus through feedback control of one or more of the process variables controlling the conditions of the dissolution testing. Random input modeling is performed to tune a PID controller for each process variable and accomplish on-line, optimally adaptive control. These process variables may include the composition (e.g., pH) of the dissolution medium; agitation via stirring paddles; agitation via primary flow rate; and/or sink conditions in the form of recycle flow of medium back into the dissolution cell.

The improved control system 200 may be considered as as expanded version of the closed loop control system shown in more generalized form in FIG. 2. In FIG. 5, the improved control system 200 is shown as a four channel device wherein each channel corresponds to a particular process variable to be optimized. Thus, four proportional-integral-derivative (PID) controllers 202, 204, 206 and 208 have as their common inputs an error signal E(t) derived as the difference between the input signal A(t) and the output signal C(t). Each PID controller also has an individual set of adjust lines taken from the group of parameter adjust lines 210. While the improved control system 200 is clearly shown as being a digital embodiment, the specific apparatus used to implement the controlling has been deemphasized—except for a few places where digital-to-analog (D/A) and analog-to-digital (A/D) converters are needed—in order to better clarify the RIM technique which is the heart of the improvement being described. The particular parameters adjusted via the lines 210 are described below. Individual outputs from the four PID controllers are routed to a corresponding number of summing junctions 212, 214, 216 and 218, respectively; each summing junction also having a pseudo-random binary signal (PRBS) applied to it from a PRBS generator 220, via a four section low pass filter 220A. Individual outputs from the four summing junctions are routed to a corresponding number of D/A converters 222, 224, 226 and 228; and are further routed via a group of lines 230 to other control elements within the parameter adjust section. A set of individual analog control signals from the four D/A's are then applied to a corresponding number of actuators 232, 234, 236 and 238—which correspond to the various pumps/motors described in connection with FIG. 1. The correspondence is as follows: the pH actuator 232 may correspond to the pump 38 and its associated modulator; the agitation actuator 234 may correspond to the stirring paddle 80 and its associated motor; the primary flow actuator 236 may correspond to the primary pump 18 and its associated modulator; and the recycle actuator 238 may correspond to the recycle pump 26 and its associated modulator. The four actuators function, as previously described, to control the process variables establishing the conditions of the dissolution testing resulting in an output concentration of the drug form detected by a spectrophotometer 242 (corresponding to the element 58 of FIG. 1). The concentration vs time profile C(t)—the desired output quantity—is digitized in an A/D converter 244 and is applied first via a path 246 to an input node 248 where it is differenced with the A(t) signals; and further via a path 250 to the inputs of four process variable tuners 252, 254, 256 and 258. The tuners are substantially identical and hence the structure and function of one only will be described. The tuners may be implemented as a discrete collection of digital circuits operating under the control of a central processor (element 56 of FIG. 1); and may also be implemented via separate, but cooperating microprocessors; and may further be embedded in the central processor 56 itself. Tuner 258, the one associated with optimizing the recycle flow rate R(t), is shown as comprised of a cross-correlator 260 to which is applied a pair of input signals on the lines 230A and 250A. The path 250A provides the C(t) signal, while the path 230A provides a combined signal containing the control signal plus the random signal—from the output of summing junction 218. The output from the cross-correlator is integrated in integrator 262, whose output is in turn applied to recycle curve element 264 which produces a process reaction curve directed to optimizing the recycle flow rate parameter. A control parameter determining element 266 receives the output from the recycle curve element 264 and periodically produces updated values for three key parameters, which are applied via an interfacing element 268, for use in the PID controller 208. These three key parameters are the overall controller gain $K_C$; the integral time $T_I$, and the derivative time $T_D$. The interested reader is referred to a 1953 published article wherein the parameter-tuning technique of the present invention is described. See, Cohen, G. H. and Coon, G. A., "Theoretical Considerations of Retarded Control," Trans. ASME, Vol. 74, 1953, pp. 827. The technique has become very well known in the control system arts and is referred to hereinafter as the "Cohen-Coon method".

In order to improve the fidelity of the bioavailability prediction when the improved control system 200 is operating in the open loop mode, it is useful to first determine the proper control parameter ($K_C$, $T_I$ and $T_D$) settings for each of the PID controllers 202, 204, 206 and 208. This is best done by random input modeling during an experimental run performed with a reference drug form in the closed loop mode of operation. The recycle rate control channel is illustrative of the method used. Superimposed on each channel control signal is a pseudo-random binary signal with an amplitude at least one standard deviation greater than the noise level in the channel and a bandwidth corresponding to ten times the bandwidth of the channel. Active electronic filtering of the output from the PRBS generator 220 by a low pass filter 220A may or may not be necessary due the possibility of auto-filtering by the mechanical damping characteristics of the actuators used. The signal output of the spectrophotometer 242 will contain the results of the control signal plus the PRBS. This signal C(t) is cross-correlated with the combined input signal (control signal plus PRBS) over a period of (illustratively) five times constants to yield a weighting function at the output of the cross-correlator 260. A process reaction curve is produced by integrating the weighting function in the integrator 262, and the control parameters ($K_C$, $T_I$ and $T_D$) are determined by the method of Cohen and Coon within the element 266. These new controller settings for each process variable are substituted into the four PID controllers and the process is repeated for another five time constants. The procedure is performed independently for each of the four PID controllers and simultaneously for all four controllers during each experimental run.

This process of controller tuning is initially performed independently (and/or in combination with one or more of the other process variables) for each process variable to obtain initial estimates of controller settings for each controller. In the course of an actual run, the controllers for each of the four process variables operate together in parallel and are returned periodically (every 5 time constants, illustratively) simultaneously to provide new updated values for the controller settings. Controller setting values obtained by his adaptive control procedure during the course of an experimental run are rejected, and previous values retained, if the proposed values are outside of a range of values for each setting which had been found to induce instability in the operation of one or more of the loops.

Although the invention has been described in terms of selected preferred embodiments and improvements to these embodiments, the invention should not be deemed limited thereto, since other embodiments and modifications will readily occur to one skilled in the art. It is therefore to be understood that the appended claims are intended to cover all such modifications as fall within the true spirit and scope of the invention.

What is claimed is:

1. Apparatus for the automated dissolution testing of products whose solubility and dissolution rate properties affect product performance comprising:
   (a) a dissolution cell having an input line, an output line, and a filtering chamber therebetween;
   (b) at least two reservoirs connected to said input line through a like number of media supply lines for providing dissolution media from said reservoirs to said filtering chamber;
   (c) first flow control means responsive to a first control signal and positioned in said input line for controlling the flow of dissolution media through said filtering chamber, and second flow control means responsive to a second control signal and positioned in at least one of said media supply lines for controlling the flow of dissolution media therethrough;
   (d) recirculating means including third flow control means responsive to a third control signal and connected to said input and output lines for controlling recirculatory flow therebetween;
   (e) system output means connected to said output line and containing means for measuring output parameters therein including a concentration parameter of particular constituents flowing therethrough, and for providing a time series of system output signals corresponding to said measured output parameters;
   (f) memory means for providing a time series of stored control signals to said apparatus; and
   (g) a multimode electronic control system having a separate feedback control channel for providing each of said first, second and third control signals, said control system connected to said first, second and third flow control means, and to said system output means, and using negative feedback circuitry in a first mode to form a difference error signal between said stored control signals and said system output signals for automatically determining said first, second and third control signals so as to continuously tend to minimize the value of said difference error signal, and further operative in a second mode for automatically providing said first, second and third control signals in the absence of said stored control signals.

2. The apparatus of claim 1 wherein said dissolution cell further comprises:
   (a) agitation means disposed within said filtering chamber and responsive to an agitation control signal for controlling the agitation rate within said chamber; and
   (b) wherein said electronic control system further comprises a separate feedback control channel for producing said agitation control signal, whereby said first, second and third control signals in combination with said agitation control signal continuously tend to minimize the magnitude of said difference error signal.

3. The apparatus of claim 2 wherein said measured output parameters include a flow parameter corresponding to the flow through said system output means.

4. The apparatus of claim 2 wherein said electronic control system includes digital algebraic subtractive circuitry for determining a flow parameter corresponding to the flow through said system output means by determining the difference between said first and third control signals.

5. The apparatus of claim 2 wherein said at least two reservoirs provide dissolution media of substantially different characteristics and said electronic control system comprises two feedback control channels for controlling the ratio of said different dissolution media by adjusting the ratio of said first and second control signals.

6. The apparatus of claim 5 wherein said at least two reservoirs contain acidic and alkaline media respectively, and said ratio of said different dissolution media constitutes a pH control.

7. The apparatus of claim 6 wherein said product is a pharmaceutical drug dosage form and said time series of stored control signals comprise in vivo dissolution profiles.

8. A method of automatic dissolution testing of soluble products having unknown dissolution profiles by comparison against known product forms having known dissolution profiles, comprising:
   (a) flowing a dissolution medium of controllable content at a controllable flow rate through a dissolution cell containing said known product form;
   (b) providing a recirculation path around said dissolution cell to provide controllable sink conditions therethrough;
   (c) measuring the concentration profile of said known product form at the output of said dissolution cell and providing a time series of output signals corresponding thereto;
   (d) providing a time series of stored signals corresponding to the known dissolution profile of said known product form;
   (e) producing a family of control signal parameters for a multimode electronic feedback control system, from an error signal formed between said output signals and said stored signals, so as to continuously tend to minimize the magnitude of said error signal;
   (f) producing a time series of process variable of control signals representative of said controllable medium content, said controllable flow rate, and said controllable sink conditions from said family of control signal parameters; and (g) flowing a dissolution medium of said controlled content at said controlled flow rate and at said controlled sink conditions through a dissolution cell containing said soluble product whereby measured concentration profiles of said soluble product are derived by said feedback control system using said produced control signal parameters and said produced process variable control signals as being predictive of subsequent usage dissolution profiles.

9. The method of claim 8 further comprising the step of providing agitation at a controllable rate within said dissolution cell and wherein said time series of process variable control signals includes signals representative of said controllable agitation rate.

10. The method of claim 9 wherein said step of flowing a dissolution medium of controllable content comprises controlling the pH of said controlled medium.

11. The method of claim 9 wherein said time series of stored signals comprise a concentration profile over a predetermined period of time.

12. The method of claim 9 wherein said soluble product is a pharmaceutical drug dosage form and said stored signals comprise in vivo dissolution (response) profiles and said predictive subsequent usage dissolution profiles comprise predictive in vivo dissolution profiles.

13. A method of simultaneously predicting in vivo dissolution profiles of a plurality of pharmaceutical drug dosage forms by comparison with a reference drug dosage form having a known in vivo dissolution profile, comprising:

(a) passing a reference dissolution medium formulated as a mixture of at least two constituents under the control of a mixture control signal through a reference dissolution cell containing said reference drug, at a flow rate controlled by a flow control signal and at an agitation rate within said dissolution cell controlled by an agitation control signal;

(b) flowing a plurality of dissolution media, each of which is formulated as a mixture of at least two constituents under the control of said mixture control signal, through a corresponding plurality of dissolution cells, each of which contains a different one of said plurality of drug dosage forms;

(c) providing a separate recirculation path around each of said dissolution cells, each path having a recirculation rate controlled responsive to a sink control signal;

(d) measuring the concentration profile of said reference drug at the output of said reference dissolution cell and providing a time series of output signals corresponding thereto;

(e) providing a time series of stored signals corresponding to the concentration profile of said reference drug;

(f) producing a set of optimized process variable control signals optimized by deriving a difference signal between said time series of output signals and said time series of stored signals; and (g) producing said mixture control signal, said flow control signal, said sink control signal and said agitation control signal such that said derived difference signal is continually minimized.

14. The method of claim 13 further comprising the step of introducing a pseudo random binary signal into a processed version of said derived difference signal to further optimize in part said optimized process variable control signals.

15. Apparatus for automatic dissolution testing of products whose solubility and dissolution rate properties affect product performance comprising:

(a) a dissolution cell having an input line, an output line, and a dissolution chamber therebetween;

(b) at least two reservoirs connected to said input line through a like number of media supply lines for providing dissolution media from said reservoirs to said dissolution chamber;

(c) first flow control means responsive to a first control signal and positioned in said input line for controlling the flow of dissolution media through said filtering chamber, and second flow control means responsive to a second control signal and positioned in at least one of said media supply lines for controlling the flow of dissolution media therethrough;

(d) recirculating means including third flow control means responsive to a third control signal and connected to said input and output lines for controlling recirculatory flow therebetween;

(e) system output means connected to said output line and containing means for measuring output parameters therein including a concentration parameter of particular constituents flowing therethrough, and for providing system output signals corresponding to said measured output parameters;

(f) memory means for providing stored control signals to said apparatus; and (g) an electronic feedback control circuit connected to said system output means, and to said memory means, and to said first, second and third flow control means, and having an input node for producing an error signal as the algebraic difference between said stored control signals and said system output signals, and further having a separate control channel for providing each of said first, second and third control signals wherein each of said control channels comprises a controller circuit for processing said error signal into one of said flow control signals.

* * * * *